United States Patent
Adelman et al.

(10) Patent No.: US 7,230,112 B2
(45) Date of Patent: *Jun. 12, 2007

(54) PROCESS FOR MAKING AMIDE ACETALS

(75) Inventors: Douglas J. Adelman, Wilmington, DE (US); Neville Everton Drysdale, Newark, DE (US); Christian Peter Lenges, Wilmington, DE (US); Mark A. Scialdone, Oxford, PA (US); Leen Tanghe, Eemegem (BE); Jozef Theresia Huybrechts, Turnhout (BE); Laura Ann Lewin, Greenville, DE (US); Robert John Barsotti, Franklinville, NJ (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 126 days.

This patent is subject to a terminal disclaimer.

(21) Appl. No.: 10/960,656

(22) Filed: Oct. 7, 2004

(65) Prior Publication Data

US 2005/0222425 A1    Oct. 6, 2005

Related U.S. Application Data

(60) Provisional application No. 60/509,885, filed on Oct. 9, 2003.

(51) Int. Cl.
*C07D 498/02* (2006.01)
(52) U.S. Cl. .................. 548/218; 106/14.05
(58) Field of Classification Search ............... 548/218; 106/14.05
See application file for complete search history.

(56) References Cited

U.S. PATENT DOCUMENTS 4,636,558 A   1/1987   Goel et al.
4,652,655 A   3/1987   Goel et al.
4,721,767 A   1/1988   Goel
4,760,178 A * 7/1988   Goel ..................... 564/30
2005/0074615 A1* 4/2005   Adelman et al. ........ 428/411.1

FOREIGN PATENT DOCUMENTS

| EP | 0 171 811 A2 | 2/1986 |
| EP | 0 267 976 | 5/1988 |
| GB | 1 203 660 | 9/1970 |
| WO | WO 9731073 | 8/1997 |
| WO | WO 2004/090056 | 10/2004 |

OTHER PUBLICATIONS

K. Burzin et. al., 4,6 Dioxa-1-aza-bicycloa3.3.ouoctane aus Iminodiaethanlen und Nitrilen, Angewandte Chemie., 1973, pp. 1055-1056, vol. 85.

Anonymous, Low Viscosity Bicyclic Amide Acetal Compounds Used as Blocked Hydroxyl-Containing Compounds in Coating Compositions, Which Provide a Long Pot Life and a Fast Drying Time, Research Disclosure, 1999, No. 427054.

International Search Report Dated Mar. 23, 2005, International Application No. PCT/US2004/033437, International Filing Date: Aug. 10, 2004.

* cited by examiner

*Primary Examiner*—Kamal A. Saeed
*Assistant Examiner*—Jason M. Nolan
(74) *Attorney, Agent, or Firm*—Kevin S. Dobson

(57) ABSTRACT

Described in this invention is a catalytic process for making amide acetals from nitrites and diethanolamines. Amide acetals can be further crosslinked by hydrolyzing the amide acetal groups, and subsequently reacting the hydroxyl groups and/or the amine functions that are formed, to crosslink the composition.

6 Claims, No Drawings

PROCESS FOR MAKING AMIDE ACETALS

CROSS-REFERENCE TO RELATED APPLICATION

This application claims priority under 35 U.S.C. §119 from U.S. Provisional Application Ser. No. 60/509,885, filed Oct. 9, 2003.

FIELD OF THE INVENTION

Described in this invention is a catalytic process for making amide acetals from nitrites and diethanolamines. Amide acetals can be further crosslinked by hydrolyzing the amide acetal groups, and subsequently reacting the hydroxyl groups and/or the amine functions that are formed, to crosslink the composition.

TECHNICAL BACKGROUND

The synthesis of bicyclic amide acetals by the reaction of a dialkanol amine, such as diethanol amine with alkyl nitriles has been reported to result in relatively low yields (30–40%) in Angew Chem. 85, (1973). U.S. Pat. No. 4,652,655 describes an improved process for preparation of bicyclic acetal amides by the reaction of an organic nitrile with a dialkanol amine wherein the reaction temperature is maintained below about 140° C. European Patent application EP 0171811 A2 describes a process for preparing bicyclic amide acetal by reacting diethanolamine and a nitrile having a formula R—C—N where R is an alkyl, aralkyl, or alicyclic group in presence of an alkali metal or an alkaline earth metal catalyst in a temperature range of 80° C. to 120° C. However, the reaction time with such catalysts is long and the conversion rate is poor.

Amide acetals have been used for example in copolymerization with polyisocyanates as disclosed in U.S. Pat. No. 4,721,767. Crosslinked amide acetal based coating compositions dry and cure rapidly without the potential problems created by VOC emissions. Such coatings can be very useful, for example, in the automotive coatings industry.

The crosslinking (curing) of polymers is an important commercial activity, useful, for example, in elastomers, in coatings, and in thermoset materials such as are used for electronics. Controlling when and under what conditions crosslinking takes place is usually critical since once a polymer is crosslinked it is usually not "workable," that is it may not be reshaped. In some applications, such as coatings and electronic applications it may be desirable or even mandatory that no lower molecular weight compounds be volatilized during or after the crosslinking of the polymers, so as not to contaminate sensitive equipment such as electronics, and/or to pollute the environment, as in the case of coatings.

Numerous ways have been found to avoid the production of volatile compounds during curing. For example, the reaction of epoxy groups with other groups such as hydroxyl groups may accomplish this result, but it is sometimes difficult to control after the ingredients are mixed. Furthermore, higher temperatures may be required for this operation. To avoid these types of problems, especially in coatings which often must be cured under conditions close to ambient conditions and which often must be stable for long periods before curing, other solutions have been found, such as the use of spiroorthoesters, see for example World Patent Application 9731073. However new and/or improved methods of crosslinking polymers are needed.

For coatings, basecoat-clearcoat systems have found wide acceptance in the past decade as automotive finishes. Continuing effort has been directed to such coating systems to improve the overall appearance, the clarity of the topcoat, and the resistance to deterioration. Further effort has been directed to the development of coating compositions having low volatile organic content (VOC). A continuing need exists for coating formulations, which provide outstanding performance characteristics after application.

In repairing damage, such as dents to auto bodies, the original coating in and around the damaged area is typically sanded or ground out by mechanical means. Some times the original coating is stripped off from a portion or off the entire auto body to expose the bare metal underneath. After repairing the damage, the repaired surface is coated, preferably with low VOC coating compositions, typically in portable or permanent low cost painting enclosures, vented to atmosphere to remove the organic solvents from the freshly applied paint coatings in an environmentally safe manner. Typically, the drying and curing of the freshly applied paint takes place within these enclosures. Furthermore, the foregoing drying and curing steps take place within the enclosure to also prevent the wet paint from collecting dirt or other contaminants in the air.

As these paint enclosures take up significant floor space of typical small auto body paint repair shops, these shops prefer to dry and cure these paints as fast as possible. More expensive enclosures are frequently provided with heat sources, such as conventional heat lamps located inside the enclosure to cure the freshly applied paint at accelerated rates. Therefore, to provide more cost effective utilization of shop floor space and to minimize fire hazards resulting from wet coatings from solvent based coating compositions, there exists a continuing need for low VOC fast curing coating formulations which cure under ambient conditions while still providing outstanding performance characteristics.

Amide acetals have been used for example in copolymerization with polyisocyanates as disclosed in U.S. Pat. No. 4,721,767. However, none of the references describe the crosslinking of amide acetal containing compositions via hydrolysis of the amide acetal groups. This invention provides amide acetal based coating compositions, which dry and cure rapidly without the potential problems created by VOC emissions.

The present invention discloses a novel catalytic process for making low color amide acetals. This process provides a rapid conversion of the reactants and also the conversion of the reactants is generally higher than reported in literature. It also discloses the use of these materials in crosslinked compositions and coatings.

SUMMARY OF THE INVENTION

This invention relates to a process for preparing amide acetal, including diamide acetals (when m is 2), and multifunctional amide acetals (when m is more than 2), represented in Formula III below, comprising contacting an organic nitrile represented by Formula I with a dialkanol amine represented by Formula II in presence of a catalyst;

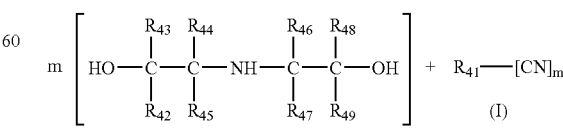

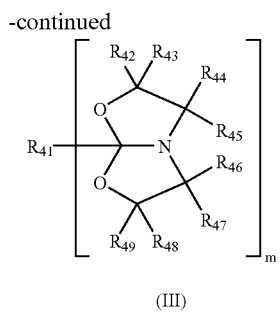

(III)

wherein m is 1, 2, 3, or 4;
wherein $R_{41}$–$R_{49}$ are independently selected from the group consisting of hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, and $C_1$–$C_{20}$ aralkyl group, said alkyl, alkenyl, alkynyl, aryl, or aralkyl each have one or more substituents selected from the group consisting of halo, alkoxy, nitrile, imino, amino, alkylamino, dialkylamino, cyano, alkoxy silane, hydroxyl, methacryloxy, isocyanato, urethane, amide acetal (multifunctional) and carbamoyl; and
wherein the catalyst is a salt of a principal metal component, wherein the principal metal component is selected from the group consisting of scandium, titanium, vanadium, chromium, manganese, iron, cobalt, nickel, copper, zinc, and cadmium.

This invention further relates to compositions of multifunctional amide acetals, of Structure III above,

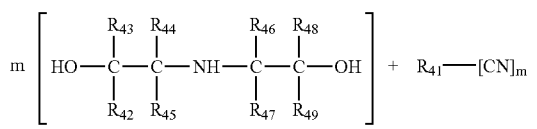

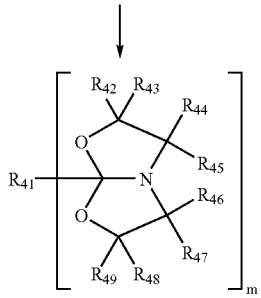

wherein m≧2.

DETAILED DESCRIPTION OF THE INVENTION

This invention relates to a process for the preparation of amide acetals.

By an amide acetal group herein is meant a group of the formula

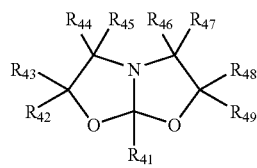

wherein $R_{41}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, nitrile, imino, amino, alkylamino, dialkylamino, cyano, alkoxy silane, hydroxyl, methacryloxy, isocyanato, urethane, amide acetal(difunctional) and carbamoyl.

In one embodiment of this invention amide acetal is made by the reaction of an appropriate dialcoholamine (not including, for example, any other hydroxyalkyl groups which may also be present in the "diol") with nitrites as shown in the reaction below with inorganic or an organic salt

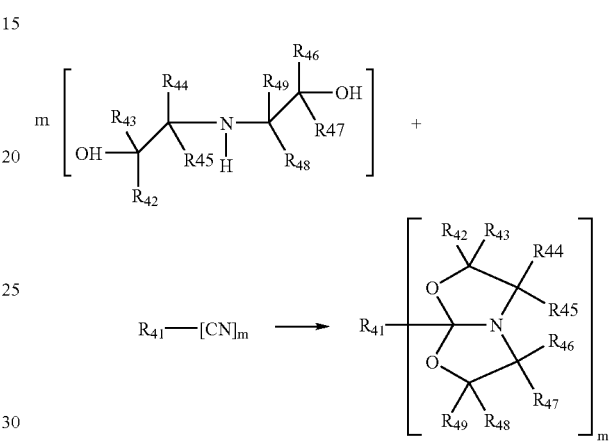

catalyst.

In the above embodiment, $R_{41}$ independently represents a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, nitrile, imino, amino, alkylamino, dialkylamino, cyano, alkoxy silane, hydroxyl, methacryloxy, isocyanato, urethane, amide acetal(difunctional and multifunctional) and carbamoyl. $R_{42}$–$R_{49}$ are as defined above.

In a preferred embodiment, the organic nitrites useful in this process include aliphatic mononitriles having from 1 to 20 carbon atoms, aromatic mononitriles having from 7 to 15 carbon atoms and alkylaromatic mononitriles having from 8 to 20 carbon atoms and aliphatic dinitriles having from 3 to 22 carbon atoms, aromatic dinitriles having from 8 to 16 carbon atoms and alkaryl dinitriles having from 9 to 21 carbon atoms. Additionally, aliphatic trinitriles having from 3 to 30 carbon atoms, aromatic trinitriles having from 6 to 36 carbon atoms, and alkaryl trinitriles having from 6 to 36 carbon atoms are useful.

The dialkanol amines useful in the process of this invention include substituted and unsubstituted dialkanol amines having the general formula HOC(R)$_2$ CH$_2$ NHCH$_2$ C(R")$_2$ OH wherein R and R" independently represent hydrogen, an alkyl group having from 1 to 10 carbon atoms or an aryl group having from 6 to 12 carbon atoms.

"Heterogeneous catalyst" refers to a catalyst that operates on reactions taking place on surfaces where the reacting species are held on the surface of the catalyst by adsorption.

A suitable base catalyst useful in the process of the invention is either a substance, which has the ability to accept protons as defined by Brönsted, or as a substance, which has an unshared electron pair with which it can form a covalent bond with an atom, molecule or ion as defined by Lewis. A further description of base catalysts and how to determine whether a particular catalyst is basic is provided in Tanabe, K., *Catalysis: Science and Technology*, Vol. 2, pg 232–273, ed. Anderson, J. and Boudart, M., Springer-Verlag, N.Y., 1981.

The catalysts employed herein may be used as powders, granules, or other particulate forms, or may be supported on an essentially inert support as is common in the art of catalysis. Selection of an optimal average particle size for the catalyst will depend upon such process parameters as reactor residence time and desired reactor flow rates Suitable supports include, but are not limited to, alumina, titania, silica, zirconia, zeolites, carbon, clays, and combinations thereof. Any method known in the art to prepare the supported catalyst can be used. The support can be neutral, acidic or basic, as long as the surface of the catalyst/support combination is basic. Preferred supports are those, which are neutral and have low surface areas. Commonly used techniques for treatment of supports with metal catalysts can be found in B. C. Gates, *Heterogeneous Catalysis*, Vol. 2, pp. 1–29, Ed. B. L. Shapiro, Texas A & M University Press, College Station, Tex., 1984.

Preferred catalysts are oxides and carbonates of a Group 1, 2, or rare earth metals, optionally supported on a suitable support, and combinations thereof. One method for preparing these catalysts is to dissolve a metal acetate salt in water. A support such as silica is wet with the solution, then calcined. The most preferred embodiment is where the metal catalyst is barium, cesium, rubidium. Other preferred catalysts include salts of organic acids such as cesium acetate, rubidium acetate, potassium acetate, barium acetate, magnesium acetate, calcium acetate, and mixtures thereof.

Preferred catalyst salts used in the above process includes salts of metals such as scandium, titanium, vanadium, chromium, manganese, iron, cobalt, nickel, copper and zinc. A preferred catalytic metal is cadmium. Another preferred catalytic metal is zinc.

A typical, but not exclusive list of catalysts which may be used alone or as mixtures for the preparation of the amide acetals of this invention include $ZnCl_2$, Zn acetate Zn pivalate, Zn stearate, $ZnBr_2$, $ZnY_2$, where Y is $C_1$–$C_{20}$ alkyl, and other catalysts as listed in Table 4 below.

Another preferred metal as the principal component of the catalyst is selected from the group consisting of palladium, ruthenium, rhenium, rhodium, iridium, platinum, compounds thereof, and combinations thereof.

A preferred catalyst content range of the supported catalyst is from about 0.01% to about 30%. A more preferred catalytic metal content range is from about 0.05% to about 2%. A further preferred catalytic metal content range is from about 0.1% to about 1%.

The process is preferably performed in the liquid phase. The process can be performed in any suitable reactor such as, but not limited to a pulse, fluidized bed, fixed bed, steady state riser reactor, and a recirculating solids reactor system.

A temperature range of from about 70° C. to about 400° C. is preferred for the processes of the invention. A temperature range of from about 80° C. to about 180° C. is further preferred. A temperature range of from about 100° C. to about 150° C. is most preferred for the above process.

Generally, the process of this invention operates at atmospheric pressure. However, the reaction can be performed in a pressure range of about 0.05 MPa to about 0.25 MPa.

The process of the present invention may be carried out in batch, sequential batch (i.e., a series of batch reactors) or in continuous mode in any of the equipment customarily employed for continuous process (see for example, H. S. Fogler, Elementary Chemical Reaction Engineering, Prentice-Hall, Inc., N.J., USA). Ammonia formed as a product is removed by conventional equipment such as scrubbing or stripping equipment, or purged using a gas stream, such as a nitrogen stream.

It will be appreciated that the selectivities and yields of product may be enhanced by additional contact with the catalyst. For example, yields and selectivities may be increased where the reactor effluent containing a mixture of reactant and product may be contacted additional times over the catalyst under the reaction conditions set forth above to enhance the conversion of reactant to product.

A significant advantage of using this process in the production of amide acetal is the ability to form a product with low color, i.e., a product with color of less than 220 Pt—Co number, preferably less than 100 Pt—Co number, and more preferably less than 70 Pt—Co number.

By polymers herein are meant those entities with number average molecular weight from about 100 to about 100,000. Preferably, the number average molecular weight of the polymers is from about 100 to about 10000.

By oligomers herein is meant those polymers, which have a number average molecular weight less than about 3000.

In the crosslinkable compositions herein, amide acetals groups are present in some form (see below), and the crosslinking reaction can be initiated when water comes in contact with these groups to hydrolyze them. By water is meant water in the pure form, moisture, moist air, moist gas or mixture of gases, or any other aqueous or non-aqueous media in which water may be present in a homogeneous or a heterogeneous mixture. Such media may be in the liquid form or the gaseous form.

When the amide acetal is simply hydrolyzed, amino hydroxy ester is formed which then converts to the amide diol as illustrated below. The amino hydroxy ester and the amide diol exist simultaneously as the reaction of conversion of the amino hydroxy ester to amide diol can be controlled by time, temperature, pH, and the urethane forming catalyst present in the reaction mixture. An advantage of the amide diol is that it demonstrates minimal yellowing in the finished product, before reacting with crosslinking agent. A rapid reaction with the crosslinking agent avoids the yellowing of the amine functionality in the product. Both of these hydrolyzed products are crosslinking agents because of the presence of their dual reactive side. In the case of the amino hydroxy ester the reactive sites are the secondary amine and the hydroxyl groups. In the case of the amide diol the reactive groups are the hydroxyls or diol:

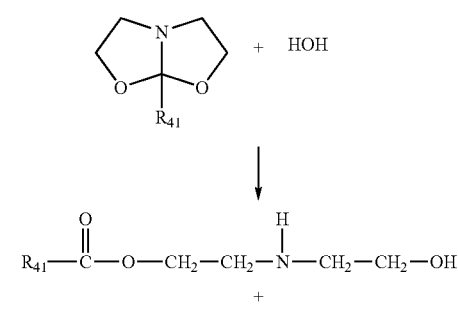

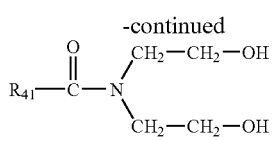

Note that in this reaction, no relatively volatile low molecular weight products are produced. Since these reactions may be acid catalyzed some of the ring opening of the amide acetal may lead to cationic polymerization rather than simple ring opening. Herein preferably the major molar portion of the amide acetal present may simply ring open and do not polymerize, more preferably at least about 75 mole percent, and especially preferably at least 90 molar percent may simply ring open and do not polymerize. The polymerization occurs generally at high temperatures. It is of course recognized that, although only one amide acetal group is shown (i.e., the case when m=1), this reaction would apply for m=2, 3 and 4 as well.

In the compositions, and in the materials used in the processes herein, the amide acetal groups may be included by a variety of methods. In one instance, the amide acetal may be included as a "monomeric" compound, which may hydrolyze, thus providing reactive hydroxyl groups.

Alternatively, the amide acetal groups may be part of a (possibly low molecular weight) polymer. For example a dihydroxy amide acetal (which has not yet been hydrolyzed) may be reacted with an excess of a diisocyanate such as bis(4-isocyanatophenyl)methane (MDI), toluene diisocyanate (TDI), hexamethylene diisocyanate (HMDI) or isophorone diisocyanate (IPDI) to form an isocyanate ended "prepolymer", which upon exposure to water undergoes hydrolysis of the amide acetal forming hydroxyl groups, which react with the remaining isocyanate groups to crosslink the polymer. Since the amide acetal often hydrolyzes faster than the isocyanate reacts with water, this is believed to be the main mode of the crosslinking reaction for this type of polymer. Other diols such as ethylene glycol or 1,4-butanediol may also be copolymerized into the (pre) polymer formed. It is noted that in this type of isocyanate containing (pre)polymer, the amide acetal group is (at least before hydrolysis) part of the main chain (not on a branch) of the polymer formed.

Alternately, the amide acetal may be functionalized, for example, via reaction of (mono)hydroxy amide acetal with isocyanate to give urethane amide acetal, or with diisocyanates, for example, 1,6-hexamethylene diisocyanate, to give diurethane diamide acetals, or Desmordur® 3300 compound from Bayer which contains multifunctional isocyanates, a triisocyanate, to give the corresponding multifunctional urethane amide acetals. Many of these compounds are novel.

An example of the crosslinking agent, or second polymer with functional groups capable of reacting with hydroxyl or secondary amines, for the amide acetal is as follows:

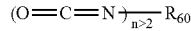

wherein $R_{60}$ is a hydrocarbyl structure.

Examples of suitable polyisocyanates include aromatic, aliphatic or cycloaliphatic di-, tri- or tetra-isocyanates, including polyisocyanates having isocyanurate structural units, such as, the isocyanurate of hexamethylene diisocyanate and isocyanurate of isophorone diisocyanate; the adduct of 2 molecules of a diisocyanate, such as, hexamethylene diisocyanate and a diol such as, ethylene glycol; uretidiones of hexamethylene diisocyanate; uretidiones of isophorone diisocyanate or isophorone diisocyanate; the adduct of trimethylol propane and meta-tetramethylxylylene diisocyanate.

Additional examples of suitable polyisocyanates include 1,2-propylene diisocyanate, trimethylene diisocyanate, tetramethylene diisocyanate, 2,3-butylene diisocyanate, hexamethylene diisocyanate, octamethylene diisocyanate, 2,2,4-trimethyl hexamethylene diisocyanate, 2,4,4-trimethyl hexamethylene diisocyanate, dodecamethylene diisocyanate, omega, omega -dipropyl ether diisocyanate, 1,3-cyclopentane diisocyanate, 1,2-cyclohexane diisocyanate, 1,4-cyclohexane diisocyanate, isophorone diisocyanate, 4-methyl-1,3-diisocyanatocyclohexane, trans-vinylidene diisocyanate, dicyclohexylmethane-4,4'-diisocyanate, 3,3'-dimethyl-dicyclohexylmethane4,4'-diisocyanate, a toluene diisocyanate, 1,3-bis(1-isocyanato1-methylethyl)benzene, 1,4-bis(1-isocyanato-1-methylethyl)benzene, 1,3-bis(isocyanatomethyl)benzene, xylene diisocyanate, 1,5-dimethyl-2,4-bis(isocyanatomethyl)benzene, 1,5-dimethyl-2,4-bis(2-isocyanatoethyl)benzene, 1,3,5-triethyl-2,4-bis (isocyanatomethyl)benzene, 4,4'-diisocyanatodiphenyl, 3,3'-dichloro-4,4'-diisocyanatodiphenyl, 3,3'-diphenyl-4,4'-diisocyanatodiphenyl, 3,3'-dimethoxy-4,4'-diisocyanatodiphenyl, 4,4'-diisocyanatodiphenylmethane, 3,3'-dimethyl-4,4'-diisocyanatodiphenyl methane, a diisocyanatonaphthalene, polyisocyanates having isocyanaurate structural units, the adduct of 2 molecules of a diisocyanate, such as, hexamethylene diisocyanate or isophorone diisocyanate, and a diol such as ethylene glycol, the adduct of 3 molecules of hexamethylene diisocyanate and 1 molecule of water (available under the trademark Desmodur® N from Bayer Corporation of Pittsburgh, Pa.), the adduct of 1 molecule of trimethylol propane and 3 molecules of toluene diisocyanate (available under the trademark Desmodur® L from Bayer Corporation), the adduct of 1 molecule of trimethylol propane and 3 molecules of isophorone diisocyanate, compounds such as 1,3,5-triisocyanato benzene and 2,4,6-triisocyanatotoluene, and the adduct of 1 molecule of pentaerythritol and 4 molecules of toluene diisocyanate. Generally the ratio of equivalents of the isocyanate to the equivalents of amine and/or hydroxyl groups, formed by the hydrolysis ring opening of the amide acetal, ranges from 0.5/1 to 3/1, preferably from 0.8/1 to 2/1, and more preferably from 1/1 to 1.8/1.

In one instance a first polymer containing intact (before hydrolysis) amide acetal groups, and a crosslinking agent containing first functional groups react with hydroxyl or secondary amine groups. The crosslinking agent may be a monomeric compound such as a diisocyanate such as MDI (diphenyl methane diisocyanate, TDI (toluene diisocyanate), HMDI (hexamethylene diisocyanate) or IPDI (isophrone diisocyanate), or an epoxy resin, or may be a polymer containing first functional groups. For example it may be (meth)acrylate copolymer containing repeat units derived from 2-isocyanatoethyl (meth)acrylate or glycidyl (meth) acrylate. It is also possible that the first polymer and the crosslinking agent are "combined" in the same polymer. For example one can copolymerize an amide acetal with 2-isocyanatoethyl (meth)acrylate or glycidyl (meth)acrylate and optionally other copolymerizable monomers. When that single polymer is exposed to moisture, presumably the amide acetal groups will hydrolyze forming amino hydroxy groups (which eventually convert to hydroxyl groups as shown previously), which in turn will react with the isocyanate, carboxylic acid anhydride, melamine, silane(s) or epoxide groups, whichever are present. These materials may be combined as a single polymer or may be more than one substance. For example, $R_{41}$ can be an alkoxy silane group having the structure $R_{50}$—Si[O(CH$_2$)$_p$H]$_3$, where each p is independently 1 to 10, and $R_{50}$ is independently selected from the group consisting of hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, and $C_1$–$C_{20}$ aralkyl. These can be used to make coating compositions.

In one preferred embodiment of this invention, a second polymer which has second functional groups capable of reacting with hydroxyl or secondary amines has a number average molecular weight less than 3000. A preferred functionality for this second polymer is isocyanate.

A specific example of the crosslinking agent, or second polymer with functional groups capable of reacting with hydroxyl or secondary amines, used here is the Desmodur® 3300 compound from Bayer. The idealized structure of Desmodur® 3300 is given as follows (also,

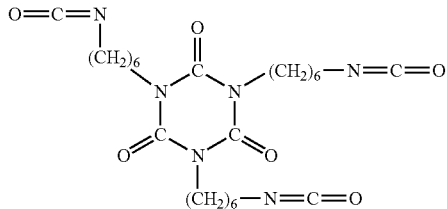

pentamer, heptamer and higher molecular weight species can be present):

The amide acetal may also be present in the polymer as part of a branch. For example, a monohydroxyl amide acetal may be converted to a (meth)acrylate ester by esterification and the resulting (meth)acrylic ester,

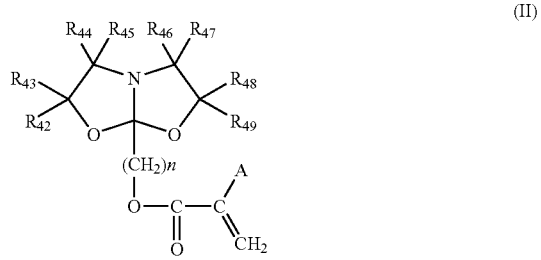

(II)

where A is H for acrylates and CH$_3$ for meth(acrylates), may be free radically copolymerized with other free radically copolymerizable monomers such as meth(acrylates) and styrenes. Analogous variations will be obvious to the skilled artisan.

Also present in these compositions, as amide acetals and the processes in which they are used, is a material having a first or second functional group which reacts with hydroxyl or secondary amine groups. This reaction should take place under the conditions chosen for the crosslinking reaction. These conditions may be ambient conditions or heating or other conditions that may be used to prod the reaction to proceed. Preferably the reaction with hydroxyl or secondary amine groups should not produce any volatile low molecular weight compounds, except those normally found in air (CO$_2$, water, etc.) Typical groups which react with hydroxyl or secondary amine groups include isocyanates (including isocyanurate trimers), epoxides, carboxylic acid anhydrides (especially those which are parts of polymers), melamine, and silane(s). Isocyanates, melamine and silane are especially preferred for coatings.

In any of the compositions herein, the polymeric materials may range from relatively low to relatively high molecular weight. It is preferred that they be of relatively low molecular weight so as to keep the viscosity of the compositions before crosslinking low, so as to avoid or minimize the need for solvent(s).

The compositions herein may contain water. It is to be understood that as the water contacts the amide acetal groups present in the composition, the amide acetal groups will start to hydrolyze, eventually leading to crosslinking of the composition. The water may be introduced in a variety of ways. For example, especially in the case of a coating the water may be introduced into the uncrosslinked or crosslinking (while the crosslinking is taking place) coating by absorption from the air. This is very convenient for making an uncrosslinked coating composition which is stable until exposed to (moist) air. Alternatively water may be mixed in a mixing head or spray mixing head (for a coating) just before crosslinking is to take place. This is particularly useful for making thicker crosslinked items such as electronic encapsulants where diffusion of moisture into a thicker section will take longer. The introduction of water can be at a point where the final shape of the polymeric crosslinked part can be formed before crosslinking takes place.

Other materials which may optionally be present in the compositions and processes include one or more solvents (and are meant to act only as solvents). These preferably do not contain groups such as hydroxyl or primary or secondary amino groups which can react with either the first or second functional groups and/or amide acetals. One or more catalysts for the hydrolysis of amide acetals may be present. These are typically Brösted acids, but these acids should not be so strong as cause substantial cationic ring opening polymerization of the amide acetals and/or epoxides which may be present. If substantial cationic ring opening polymerization of amide acetal groups takes place, this can often lead to premature crosslinking of the composition. The same caveats may be said for any catalysts which may be present which catalyze the reaction of hydroxyl groups or the amino hydroxy groups with the first or second functional groups. What these catalysts may be will depend on what the first or second functional group(s) present are. Such catalysts are known in the art. Suitable concentrations for the acid hydrolysis catalyst is in the range of 0.001 to 5 percent, preferably 0.05 to 4 percent, and more preferably from 0.1 to 3 percent, all in weight percent based on the total solids of the film forming components.

Some of the suitable catalysts for polyisocyanate can include one or more tin compounds, tertiary amines or a combination thereof; and one or more aforedescribed acid catalyst. Suitable tin compounds include dibutyl tin dilaurate, dibutyl tin diacetate, stannous octoate, and dibutyl tin oxide. Dibutyl tin dilaurate is preferred. Suitable tertiary amines include triethylene diamine. One commercially available catalyst that can be used is Fastcat® 4202-dibutyl tin dilaurate sold by Elf-AtoChem North America, Inc. Philadelphia, Pa. It is acknowledged that one skilled in the art could use acetic acid or such weak acids to block the activity of the catalyst. Suitable concentrations of amine and tin catalysts are in the range of 0.001 to 5 percent, preferably 0.005 to 2 percent, and more preferably from 0.05 to 1 percent of the catalyst, all in weight percent based on the total weight of the crosslinkable components.

The present compositions, and the process for making them crosslinked, are useful as encapsulants, sealants, and coatings. The coating composition of this invention can be used as a clear coat that is applied over a pigmented base coat that may a pigmented version of the composition of this invention or another type of a pigmented base coat. The clear coating can be in solution or in dispersion form.

Typically, a clear coating is then applied over the base coating before the base coating is fully cured, this basecoat may be wet as in a so called "wet-on-wet process" or physically dry to the touch, as is common in refinish applications, and then the base coating and clear coating are then fully cured at ambient temperatures or can be cured by heating to elevated temperatures of 40° C. to 100° C. for 15 to 45 minutes. The base coating and clear coating preferably have a dry coating thickness ranging from 25 to 75 microns and 25 to 100 microns, respectively.

By "crosslinker functionality" is meant is the average number of functional groups per molecule. If the functionality of the crosslinker is too low, disruption of the basecoat flake orientation may occur. This disruption is measured by flop. The higher the value of flop the lower the amount of flake orientation disruption. Less disruption of the flake orientation is seen when isocyanate is used as the crosslinker, when the HMDI isocyanurate trimer component of a crosslinker has >3.1 average functionality and a viscosity at 100% solids at 23 C of >700 mPas, preferably >900 mPas, and most preferably >1000 mpas. These values are measured with a color measurement device and compared to a commercial standard. The isocyanate composition may be a mixture of HMDI isocyanurate trimer and IPDI type isocyanaurate trimer in the range of 100% HMDI/0% IPDI to 40% HMDI/60% IPDI by weight of solids of the isocyanates, preferably 85% HMDI/15% IPDI to 50% HMDI/50% IPDI, and more preferably 75% HMDI/25% IPDI to 50% HMDI/50% IPDI.

The novel coating composition may be used as a base coat or as a pigmented monocoat topcoat. Both of these compositions require the presence of pigments. Typically, a pigment-to-binder ratio of 0.1/100 to 200/100 is used depending on the color and type of pigment used. The pigments are formulated into mill bases by conventional procedures, such as, grinding, sand milling, and high speed mixing. Generally, the mill base comprises pigment and a binder or a dispersant or both in a solvent or aqueous medium. The mill base is added in an appropriate amount to the coating composition with mixing to form a pigmented coating composition.

Any of the conventionally-used organic and inorganic pigments, such as, white pigments, like, titanium dioxide, color pigments, metallic flakes, such as, aluminum flake, special effects pigments, such as, coated mica flakes, coated aluminum flakes and the like and extender pigments can be used. It may be desirable to add flow control additives.

The novel coating composition may be used as a primer in which case typical pigments used in primers would be added, such as, carbon black, barytes, silica, iron oxide and other pigments that are commonly used in primers in a pigment-to-binder ratio of 10/100 to 300/100.

The coating composition can be applied by conventional techniques, such as, spraying, electrostatic spraying, dipping, brushing, and flow coating.

The coating composition is particularly useful for the repair and refinish of automobile bodies and truck bodies and parts as a clear coat, pigmented base coat, or as a primer. The novel composition has uses for coating any and all items manufactured and painted by automobile sub-suppliers, frame rails, commercial trucks and truck bodies, including but not limited to beverage bodies, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, large commercial aircraft and small pleasure aircraft, pleasure vehicles, such as, snow mobiles, all terrain vehicles, personal watercraft, motorcycles, and boats. The novel composition also can be used as a coating for industrial and commercial new construction and maintenance thereof; cement and wood floors; walls of commercial and residential structures, such as, office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signs; fiberglass structures; sporting goods; and sporting equipment.

An advantage of the present materials and processes in encapsulants and sealants is that when amide acetals are used in crosslinking reactions the resulting product does not shrink, or shrink as much as usual in a typical crosslinking reaction. This means any volume to be filled by the crosslinked material will be more reliably filled with a reduced possibility of voids being present due to shrinkage during crosslinking.

For whatever uses they are put to, the compositions, and the materials used in the processes described herein may contain other materials which are conventionally used in such uses. For example, for use as encapsulants and sealants the composition may contain fillers, pigments, and/or antioxidants.

For coatings there may be a myriad of other ingredients present, some of which are described below. In particular there may be other polymers (especially of low molecular weight, "functionalized oligomers") which are either inert or have functional group(s) other than those that may act as the materials comprising amide acetals and also react with other reactive materials in the coating composition.

Representative of the functionalized oligomers that can be employed as components or potential crosslinking agents of the coatings are the following:

Acid Oligomers: The reaction product of multifunctional alcohols such as pentaerythritol, hexanediol, trimethylol propane, and the like, with cyclic monomeric anhydrides such as hexahydrophthalic anhydride, methylhexahydrophthalic anhydride, and the like.

Hydroxyl Oligomers: The above acid oligomers further reacted with monofunctional epoxies such as butylene oxide, propylene oxide, and the like.

Anhydride Oligomers: The above acid oligomers further reacted with ketene.

Silane Oligomers: The above hydroxyl oligomers further reacted with isocyanato propyltrimethoxy silane.

Epoxy Oligomers: The diglycidyl ester of cyclohexane dicarboxylic acid, such as Araldite® CY-184 from Ciba Geigy, and cycloaliphatic epoxies, such as ERL®-4221, and the like from Union Carbide.

Aldimine Oligomers: The reaction product of isobutyraldehyde with diamines such as isophorone diamine, and the like.

Ketimine Oligomers: The reaction product of methyl isobutyl ketone with diamines such as isophorone diamine.

Melamine Oligomers: Commercially available melamines such as CYMEL® 1168 from Cytec Industries, and the like.

AB-Functionalized Oligomers: Acid/hydroxyl functional oligomers made by further reacting the above acid oligomers with 50%, based on equivalents, of monofunctional epoxy such as butylene oxide or blends of the hydroxyl and acid oligomers mentioned above or any other blend depicted above.

CD-Functionalized Crosslinkers: Epoxy/hydroxyl functional crosslinkers such as the polyglycidyl ether of Sorbitol DCE-358® from Dixie Chemical or blends of the hydroxyl oligomers and epoxy crosslinkers mentioned above or any other blend as depicted above.

The compositions of this invention may additionally contain a binder of a noncyclic oligomer, i.e., one that is linear or aromatic. Such noncyclic oligomers can include, for instance, succinic anhydride- or phthalic anhydride-derived moieties in the Acid Oligomers: such as described above.

Preferred functionalized oligomers have weight average molecular weight not exceeding about 3,000 with a polydispersity not exceeding about 1.5; more preferred oligomers have molecular weight not exceeding about 2,500 and polydispersity not exceeding about 1.4; most preferred oligomers have molecular weight not exceeding about 2,200, and polydispersity not exceeding about 1.25. Particularly useful oligomers are those covered in U.S. Pat. No. 6,221,494 B1, which is hereby incorporated by reference in its entirety. Typically, compositions will comprise from about 20 to about 80 weight percent of the functionalized oligomer based on the total weight of amide acetal-containing compound in the coating. Preferably compositions will comprise from about 30 to about 70 weight percent of the functionalized oligomer based on the total weight of the amide acetal-containing compound in the coating. More preferably compositions will comprise from about 40 to about 60 weight percent of the functionalized oligomer based on the total weight of amide acetal-containing compound in the coating. Other additives also include polyaspartic esters, which are the reaction product of diamines, such as, isopherone diamine with dialkyl maleates, such as, diethyl maleate.

The coating compositions may be formulated into high solids coating systems dissolved in at least one solvent. The solvent is usually organic. Preferred solvents include aromatic hydrocarbons such as petroleum naphtha or xylenes; ketones such as methyl amyl ketone, methyl isobutyl ketone, methyl ethyl ketone or acetone; esters such as butyl acetate or hexyl acetate; and glycol ether esters such as propylene glycol monomethyl ether acetate.

The coating compositions can also contain a binder of an acrylic polymer of weight average molecular weight greater than 3,000, or a conventional polyester such as SCD®-1040 from Etna Product Inc. for improved appearance, sag resistance, flow and leveling and such. The acrylic polymer can be composed of typical monomers such as acrylates, methacrylates, styrene and the like and functional monomers such as hydroxy ethyl acrylate, glycidyl methacrylate, or gamma methacrylylpropyl trimethoxysilane and the like.

The coating compositions can also contain a binder of a dispersed acrylic component which is a polymer particle dispersed in an organic media, which particle is stabilized by what is known as steric stabilization. Hereafter, the dispersed phase or particle, sheathed by a steric barrier, will be referred to as the "macromolecular polymer" or "core". The stabilizer forming the steric barrier, attached to this core, will be referred to as the "macromonomer chains" or "arms".

The dispersed polymer contains about 10 to 90%, preferably 50 to 80%, by weight, based on the weight of the dispersed polymer, of a high molecular weight core having a weight average molecular weight of about 50,000 to 500,000. The preferred average particle size is 0.1 to 0.5 microns. The arms, attached to the core, make up about 10 to 90%, preferably 10 to 59%, by weight of the dispersed polymer, and have a weight average molecular weight of about 1,000 to 30,000, preferably 1,000 to 10,000. The macromolecular core of the dispersed polymer is comprised of polymerized acrylic monomer(s) optionally copolymerized with ethylenically unsaturated monomer(s). Suitable monomers include styrene, alkyl acrylate or methacrylate, ethylenically unsaturated monocarboxylic acid, and/or silane-containing monomers. Such monomers as methyl methacrylate contribute to a high Tg (glass transition temperature) dispersed polymer, whereas such "softening" monomers as butyl acrylate or 2-ethylhexylacrylate contribute to a low Tg dispersed polymer. Other optional monomers are hydroxyalkyl acrylates or methacrylates or acrylonitrile. Optionally, the macromolecular core can be crosslinked through the use of diacrylates or dimethacrylates such as allyl methacrylate or post reaction of hydroxyl moieties with polyfunctional isocyanates. The macromonomer arms attached to the core can contain polymerized monomers of alkyl methacrylate, alkyl acrylate, each having 1 to 12 carbon atoms in the alkyl group, as well as glycidyl acrylate or glycidyl methacrylate or ethylenically unsaturated monocarboxylic acid for anchoring and/or crosslinking. Typically useful hydroxy-containing monomers are hydroxy alkyl acrylates or methacrylates as described above.

The coating compositions can also contain conventional additives such as pigments, stabilizers, rheology control agents, flow agents, toughening agents and fillers. Such additional additives will, of course, depend on the intended use of the coating composition. Fillers, pigments, and other additives that would adversely effect the clarity of the cured coating will not be included if the composition is intended as a clear coating.

The coating compositions are typically applied to a substrate by conventional techniques such as spraying, electrostatic spraying, roller coating, dipping or brushing. As mentioned above atmospheric moisture may "diffuse" into the coating and cause curing, or alternatively just before the coating is applied it is mixed with an appropriate amount of water, as in a mixing spray head. Under these latter conditions it is important to apply the coating before it crosslinks. The present formulations are particularly useful as a clear coating for outdoor articles, such as automobile and other vehicle body parts. The substrate is generally prepared with a primer and or a color coat or other surface preparation prior to coating with the present compositions.

A layer of a coating composition is cured under ambient conditions in the range of 30 minutes to 24 hours, preferably in the range of 30 minutes to 3 hours to form a coating on the substrate having the desired coating properties. It is understood that the actual curing time depends upon the thickness of the applied layer and on any additional mechanical aids, such as, fans that assist in continuously flowing air over the coated substrate to accelerate the cure rate. If desired, the cure rate may be further accelerated by baking the coated substrate at temperatures generally in the range of from about 60° C. to 150° C. for a period of about 15 to 90 minutes. The foregoing baking step is particularly useful under OEM (Original Equipment Manufacture) conditions.

EXPERIMENTAL

Experiment 1

Preparation of Amide Acetals

All catalysts used for the reactions in the following examples were obtained from Aldrich Chemical Co., Milwaukee, Wis. 53201. Diisopropanolamine was obtained from ChemCentral Co., Charlotte, N.C. Dodecane nitrile was obtained from Akzo Nobel Co., McCook, Ill. (the Arneel 12 brand) and from International Flavors & Fragrances, Hazlet, N.J. (the Clonal 03-5223 brand).

The analysis on the resulting product was done with Gas Chromatography equipped with a packed column and a thermal conductivity detector. The unit was calibrated using an internal standard (dodecane) method as described by McNair, H. M. and E. J. Bonelli in Basic Gas Chromatography, Varian Aerograph, Walnut Creek, Calif., 1969.

For some applications, the color of the product must be minimized. Reactor batch and product color analyses were done using a UV spectrophotometer and ASTM method D5386-93b. The result is given as a Pt—Co number and is an indication of the yellowness of the sample. The lower the number, the less yellow is the sample. A value of zero is comparable to the color of pure water. In the present invention, materials with Pt—Co values of less than or equal to 220 are useful, with values of less than or equal to 100 preferred, and values of less than or equal to 70 more preferred.

Experiment 2

Preparation of Copper Aluminosilicate Catalyst

Sodium aluminosilicate, $NaAlO_2(SiO_2)_2 \cdot H_2O$, was treated with a 0.5M solution of copper formate, the mixture heated at 80° C. for 30 minutes, then filtered and washed with water to produce a blue powder that was dried at 200° C.

EXAMPLE 1

Preparation of 1-Aza-(3,7-dimethyl-5-n-undecyl)-4,6-dioxabicyclo[3,3,0]octane

Undecyl nitrile (50.00 g, 0.2750 mol), diisopropanolamine (33.25 g, 0.2500 mol) and cadmium acetate dihydrate (1.66 g, 0.0062 mol) were contacted in a three-neck flask equipped with stirrer and input for nitrogen. The reactor contents were heated to and held at 130° C. for about 20 hours under nitrogen atmosphere.

The reaction mixture was cooled to room temperature. The resulting clear solution was fractionally vacuum-distilled yielding four fractions given below. Approximately 10 mL of material remained as residue in the reaction vessel. Based on the fourth fraction, this corresponds to a 70% yield of product.

TABLE 1

| Fraction | Weight (g) | Comment |
|---|---|---|
| 1. | 6.64 | Mixture of product and unreacted starting materials |
| 2. | 1.95 | Mixture of product and unreacted starting materials |
| 3. | 0.74 | Mixture of product and unreacted starting materials |
| 4. | 52.44 | all product-1-Aza-(3,7-dimethyl-5-n-undecyl)-4,6-dioxabicyclo[3,3,0]octane |

EXAMPLE 2

Preparation of 1-Aza-(3,7-dimethyl-5-n-undecyl)-4,6-dioxabicyclo[3,3,0]octane

Undecyl nitrile (50.00 g, 0.2750 mol), diisopropanolamine (33.25 g, 0.2500 mol) and cadmium chloride (1.14 g, 0.0062 mol) were contacted in a three-neck flask equipped with stirrer and an input for nitrogen. The reactor contents were heated to and held at 130° C. for about 20 hours under a nitrogen atmosphere.

The reaction mixture was cooled to room temperature. The resulting clear solution was fractionally vacuum-distilled yielding four fractions. Approximately 10 mL of material remained as residue in the reaction vessel. Based on the third and the fourth fraction, this corresponds to about 56% yield of product. For this reaction approximately 15 mL of residue in the reactor were not analyzed.

TABLE 2

| Fraction | Weight (g) | Comment |
|---|---|---|
| 1. | 10.41 | Mixture of product and unreacted starting materials |
| 2. | 5.84 | Mixture of product and unreacted starting materials |
| 3. | 9.32 | all product-1-Aza-(3,7-dimethyl-5-n-undecyl)-4,6-dioxabicyclo[3,3,0]octane |
| 4. | 32.31 | all product-1-Aza-(3,7-dimethyl-5-n-undecyl)-4,6-dioxabicyclo[3,3,0]octane |

EXAMPLE 3

Preparation of 1-Aza-(3,7-dimethyl-5-n-undecyl)-4,6-dioxabicyclo[3,3,0]octane

Undecyl nitrile (93.6 g, 0.513 mol), diisopropanolamine (67.5 g, 0.507 mol) and cadmium acetate dihydrate (2.71 g, 0.010 mol) were contacted in a three-neck flask equipped with stirrer and an input for nitrogen. The reactor contents were heated to and held at and held at 130° C. for 22 hours under a nitrogen atmosphere. The reaction mixture was cooled to room temperature. The resulting solution had a Pt—Co# of 105. Gas chromatographic analysis of the reactor contents indicated a final conversion of 89.1% of the nitrile to the desired product 1-Aza-(3,7-dimethyl-5-n-undecyl)-4,6-dioxabicyclo[3,3,0]octane.

EXAMPLE 4

Preparation of 1-Aza-(3,7-dimethyl-5-n-undecyl)-4, 6-dioxabicyclo[3,3,0]octane Undecyl nitrile (92.8 g, 0.509 mol), diisopropanolamine (67.7 g, 0.508 mol) and zinc acetate (1.87 g, 0.010 mol) were contacted in a three-neck flask equipped with stirrer and an input for nitrogen. The reactor contents were heated to and held at 130° C. for 5 hours and then at 150° C. for an additional about 18 hours under a nitrogen atmosphere.

The reaction mixture was cooled to room temperature. The resulting solution had a Pt—Co# of 81 and gas chromatographic analysis indicated a conversion of 82.2% of the nitrile to the desired product.

EXAMPLE 5

Preparation of 1-Aza-(3,7-dimethyl-5-n-undecyl)-4, 6-dioxabicyclo[3,3,0]octane Dodecane nitrile (83.3 g, 0.457 mol), diisopropanolamine (61.0 g, 0.458 mol) and zinc stearate (5.67 g, 0.009 mol) were contacted in a 250 mL three-neck flask equipped with stirrer and an input for nitrogen. The reactor contents were heated to and held at 150° C. for 8.75 hours under a nitrogen atmosphere.

The reaction mixture was cooled to room temperature. Gas chromatographic analysis of the reactor contents indicated a nitrile conversion of 75.8%. The batch was heterogeneous so Pt—Co# was not measured.

EXAMPLE 6

Preparation of 1-Aza-(3,7-dimethyl-5-n-undecyl)-4, 6-dioxabicyclo[3,3,0]octane Dodecane nitrile (92.5 g, 0.507 mol), diisopropanolamine (67.5 g, 0.507 mol) and zinc oxide (0.814 g, 0.010 mol) were contacted in a 250 mL three-neck flask equipped with stirrer and an input for nitrogen. The reactor contents were heated to and held at 150° C. for 8 hours under nitrogen atmosphere.

The reaction mixture was cooled to room temperature. Gas Chromatographic analysis of the reactor contents indicated a nitrile conversion of 8.9%. The batch was heterogeneous so no Pt—Co# value was measured.

EXAMPLE 7

Preparation of 1-Aza-(3,7-dimethyl-5-n-undecyl)-4, 6-dioxabicyclo[3,3,0]octane Dodecane nitrile (93.0 g, 0.51 mol), diisopropanolamine (67.5 g, 0.507 mol) and zinc chloride (1.364 g, 0.010 mol) were contacted in a 250 ml three-neck flask equipped with stirrer and an input for nitrogen. The reactor contents were heated to and held at 150° C. for 12 hours under a nitrogen atmosphere.

The reaction mixture was cooled to room temperature. Gas Chromatographic analysis of the reactor contents indicated a nitrile conversion of 52.4%. UV color analysis at 12 hours yielded a Pt—Co# of 130.

EXAMPLE 8

Preparation of 1-Aza-(3,7-dimethyl-5-n-undecyl)-4, 6-dioxabicyclo[3,3,0]octane Dodecane nitrile (93.8 g, 0.514 mol), diisopropanolamine (68.2 g, 0.512 mol) and zinc nitrate (2.975 g, 0.010 mol) were placed in a 250 ml three neck flask equipped with stirrer and an input for nitrogen. The reactor contents were heated to and held at 150° C. for 7 hours under nitrogen atmosphere.

The reaction mixture was cooled to room temperature. Gas Chromatographic analysis of the reactor contents indicated a nitrile conversion of 40.9%. UV color analysis at 7 hours yielded a Pt/Co value of 178.

EXAMPLE 9

Preparation of 1-Aza-(3,7-dimethyl-5-n-undecyl)-4, 6-dioxabicyclo[3,3,0]octane Dodecane nitrile (92.7 g, 0.508 mol), diisopropanolamine (67.6 g, 0.508 mol) and zinc sulfate monohydrate (1.797 g, 0.010 mol) were placed in a 250 ml three-neck flask equipped with stirrer and an input for nitrogen. The reactor contents were heated to and held at 150° C. for 8 hours under nitrogen atmosphere.

The reaction mixture was cooled to room temperature. Gas Chromatographic analysis of the reactor contents indicated a nitrile conversion of 25.3%. The batch was heterogeneous so no Pt—Co# value was measured.

EXAMPLE 10

Preparation of 1-Aza-(3,7-dimethyl-5-n-undecyl)-4, 6-dioxabicyclo[3,3,0]octane Dodecane nitrile (92.7 g, 0.508 mol), diisopropanolamine (67.6 g, 0.508 mol) and zinc acetate (1.837 g, 0.010 mol) were contacted in a 250 mL three-neck flask equipped with stirrer and an input for nitrogen. The reactor contents were heated to and held at 150° C. for 8.45 hours under nitrogen atmosphere.

The reaction mixture was cooled to room temperature. Gas Chromatographic analysis of the reactor contents indicated a nitrile conversion of 72.7%. UV color analysis at 8.45 hours yielded a Pt/Co# of 64.

Additionally, a comparison was made of dodecane nitrile conversion using zinc acetate [ZnAc] and sodium acetate [NaAc] as catalyst. The above method was used, and the conversion was measured at various times. The conversions, measured by gas chromatographic anaylsis, are shown in Table 3 below, and indicate that the use of zinc acetate provides higher conversion of dodecane nitrile

TABLE 3

| 150° C. Batch Temperature Time (hr) | ZnAc = 1.10 wt % or 0.055 M Dodecane Nitrile Conversion | NaAc = 0.27 wt % or 0.11 M Dodecane Nitrile Conversion |
|---|---|---|
| 0 | 0 | 0 |
| 5 | 0.50 | 0.07 |
| 10 | 0.68 | 0.12 |
| 15 | 0.76 | 0.16 |
| 20 | 0.80 | 0.21 |

EXAMPLE 11

Preparation of 1-Aza-(3,7-dimethyl-5-n-undecyl)-4,6-dioxabicyclo[3,3,0]octane Dodecane nitrile (93.1 g, 0.511 mol), diisopropanolamine (67.5 g, 0.507 mol) and zinc trifluoromethanesulfonic acid (3.71 g, 0.010 mol) were contacted in a 250 mL three-neck flask equipped with stirrer and an input for nitrogen. The reactor contents were heated to and held at 150° C. for 8.75 hours under nitrogen atmosphere.

The reaction mixture was cooled to room temperature. Gas Chromatographic analysis of the reactor contents indicated a nitrile conversion of 32.4%. UV color analysis at 8.75 hours yielded a Pt/Co# of 220.

EXAMPLE 12

Preparation of 1-Aza-(3,7-dimethyl-5-n-undecyl)-4,6-dioxabicyclo[3,3,0]octane Dodecane nitrile (92.9 g, 0.509 mol), diisopropanolamine (67.6 g, 0.507 mol) and diethyl zinc (1.240 g, 0.010 mol) were contacted in a 250 mL three-neck flask equipped with stirrer and an input for nitrogen. The reactor contents were heated to and held at 150° C. for 8.45 hours under nitrogen atmosphere.

The reaction mixture was cooled to room temperature. Gas Chromatographic analysis of the reactor contents indicated a nitrile conversion of 52.4%. UV color analysis at 8.45 hours yielded a Pt/Co# of 149.

EXAMPLE 13

Preparation of 1-Aza-(3,7-dimethyl-5-n-undecyl)-4,6-dioxabicyclo[3,3,0]octane Dodecane nitrile (1934. g, 10.61 mol), diisopropanolamine (1558. g, 11.7 mol) and zinc acetate (39.20 g, 0.2140 mol) were place in a 5 L three-neck flask equipped with stirrer and an input for nitrogen. The reactor contents were heated to and held at 140° C. for 17.2 hours under nitrogen atmosphere.

The reaction mixture was cooled to room temperature. Gas Chromatographic analysis of the reactor contents indicated a nitrile conversion of 74.6%. UV color analysis at 17.2 hours yielded a Pt/Co# of 43.

The unreacted nitrile and amine were removed via fractional distillation by raising the reactor temperature to 155° C. and lowering the pressure to 1 mm Hg ($1.33 \times 10^{-4}$ MPa). Product 1-Aza-(3,7-dimethyl-5-n-undecyl)-4,6-dioxabicyclo[3,3,0]octane was recovered by raising the temperature to 166° C. while maintaining the pressure at 1 mm Hg ($1.33 \times 10_{-4}$ MPa). A total of about 1878 g of product was recovered. A residue of 283 g remained in the reactor. This is about 8 weight percent of the initial charge.

EXAMPLE 14

Preparation of 1-Aza-(3,7-dimethyl-5-n-undecyl)-4,6-dioxabicyclo[3,3,0]octane Dodecane nitrile (6791. g, 37.45 mol), diisopropanolamine (5992. g, 44.99 mol) and zinc acetate (145.0 g, 0.790 mol) were placed in a 22 L three-neck flask equipped with stirrer and an input for nitrogen. The reactor contents were heated to and held at 140° C. for 21.3 hours under nitrogen atmosphere.

The reaction mixture was cooled to room temperature. Gas Chromatographic analysis of the reactor contents indicated a nitrile conversion of 73.5%. UV color analysis at 21.3 hours yielded a Pt/Co# of 78.

The unreacted nitrile and amine were removed via fractional distillation by raising the reactor temperature to 165° C. and lowering the pressure to 1 mm Hg ($1.33 \times 10^{-4}$ MPa). Product 1-Aza-(3,7-dimethyl-5-n-undecyl)-4,6-dioxabicyclo[3,3,0]octane was recovered by raising the temperature to 179° C. while maintaining the pressure at 1 mm Hg ($1.33 \times 10^{-4}$ MPa). A total of about 7937 g of product was recovered which represents a nitrile conversion of 71.4%. A residue of 882 g remained in the reactor which is 5.64 Wt % of the initial reactant charge.

TABLE 4

Nitrile conversion at 7 hours; T = 140° C. and catalyst = 0.056 M of original charge

| Example No. | Catalyst | Pt-Co# | % Nitrile Conversion |
|---|---|---|---|
| 5. | Zinc Stearate | NA | 74.3 |
| 6. | Zinc Oxide | NA | 17.6 |
| 7. | Zinc Chloride | 110 | 46.4 |
| 8. | Zinc Nitrate | 178 | 40.9 |
| 9. | Zinc Sulfate Monohydrate | NA | 25.3 |
| 10. | Zinc Acetate | 62 | 65.0 |
| 11. | Zinc Trifluoromethanesulfonic acid | 179 | 32.9 |
| 12. | Diethyl Zinc | 80 | 45.1 |
| 13. | Zinc Acetate | 45 | 52.0 |

EXAMPLE 15

Bis-amide acetal of adiponitrile

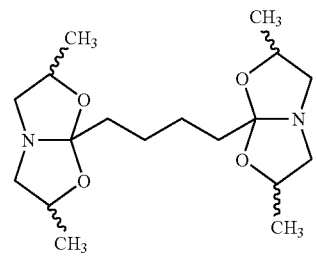

Adiponitrile (44.40 g, 0.4115 mol), diisopropanolamine (109.97 g, 0.8266 mol), para-xylene (100 mL) and zinc acetate dihydrate (4.00 g, 0.0183 mol) were placed in a three neck round bottom flask equipped with a stirrer and nitrogen bleed. The reactor contents were heated to and held at 140° C. for about 65 hours. The para-xylene was removed at reduced pressure from the cooled golden yellow reaction mixture, giving a yield of about 92.4% (129.29 g). NMR analyses of the resulting product showed desired material containing a very small amount of the half-amide acetal of adiponitrile.

EXAMPLE 16

Tri-amide acetals of 1,3,6-hexanetricarbonitrile

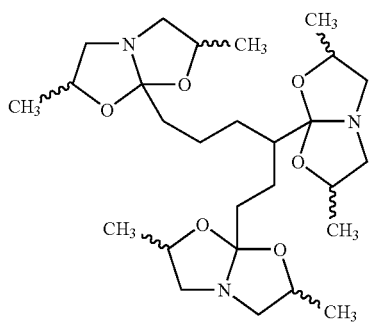

1,3,6-hexanetricarbonitrile (64.40 g, 0.40 mol), diisopropanolamine (164.92 g, 1.24 mol), para-xylene (100 mL), and zinc acetate dihydrate (6.1 g, 0.0279 mol) were placed in a three neck round bottom flask equipped with a stirrer and nitrogen bleed. The reactor contents were heated to and held at 140° C. for about 68 hours. The para-xylene was removed at reduced pressure from the cooled golden brown reaction mixture, 195.28 g, 93.3% yield. NMR analyses of the resulting product showed the desired material.

EXAMPLE 17

Heterogeneous Catalyst-based Preparation of 1-Aza-(3,7-dimethyl-5-n-undecyl)-4,6-dioxabicyclo[3,3,0]octane Undecyl nitrile (100.0 g, 0.550 mol), diisopropanolamine (66.5 g, 0.5 mol) and copper aluminosilicate (10.0 g) were placed in a three neck round bottom flask equipped with a stirrer, reflux condenser and a nitrogen bleed. The reactor contents were heated to and held at 150° C. for about 54 hours, at which stage NMR analyses indicated that the reaction was about 60–70% complete. Vacuum distillation afforded desired product in a yield of 74.89% (111.22 g).

EXAMPLE 18

Preparation of fluorinated amide acetals

Perfluorooctylnitrile (50.0 g, 0.1259 mol), diisopropanolamine (16.83 g, 0.1265 mol), meta-xylene (30.62 g) and zinc acetate dihydrate (0.61 g, 0.0028 mol) were placed in an oven dried round bottom flask equipped with stirrer, reflux condenser, and a nitrogen bleed. The reactor contents were heated to and held at 148° C. for about 66 hours. The resulting material was cooled to room temperature and the xylene removed under vacuum, and then fractionally vacuum distilled yielding 19.54 g of the desired material; boiling point 103–110° C. at 2 torr.

EXAMPLE 19–26

Preparation of 1-Aza-(3,7-dimethyl-5-n-decyl)-4,6-dioxabicyclo[3,3,0]octane

General Procedure for Examples 19–26: Undecane nitrile (5.7 g, 0.03 mol), di-isopropanolamine (5.02 g, 0.04 mol) and the catalyst (0.002 mol) were placed in a 30 ml reaction vessel equipped with stirrer under a nitrogen atmosphere. The reactor contents were heated to and held at 150° C. Samples of the reaction mixture were taken after 6 hours and 24 hours reaction time. These samples were analyzed using Gas Chromatographic analysis.

| Example | Catalyst | % Nitrile Conversion | |
|---|---|---|---|
| | | 6 hrs | 24 hrs |
| 19 | Copper(II) Pivalate | 54% | 73% |
| 20 | Copper(II) Chloride | 8% | 19% |
| 21 | Mercuric Acetate | 5% | 14% |
| 22 | Cobalt (II) Iodide | 5% | 12% |
| 23 | Cobalt (II) Carbonate | 29% | 35% |
| 24 | Copper(I) Bromide | 11% | 22% |
| 25 | Copper(II) Acetylacetonate | 35% | 9% |
| 26 | Iron(III)acetylacetonate | 2% | 14% |

EXAMPLE 27

Amino Amide Acetal 5-(2,6-Dimethyl-tetrahydro-oxazolo[2,3-b]oxazol-7a-yl)-pentamine

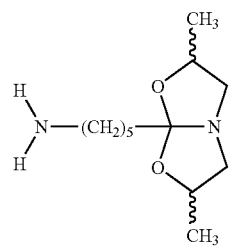

Di-isopropanolamine (133.0, 1.0 mol), 6-aminocapronitrile (112.0 g, 1.0 mol), and zinc acetate dihydrate (5.475 g, 0.025 mol) were placed in an oven dried round bottom flask equipped with stirrer, reflux condenser, and a nitrogen bleed. The reaction content was heated to 130–140° C. for ~16 hours. The resulting material was cool to room temperature and a vacuum distillation apparatus attached. The fractions boiling between 136–210° C. at 0.9–7.0 torr was collected, which NMRs analysis showed to be mostly unreacted starting materials. NMRs analysis of the material remaining in the reaction vessel showed it to be all of the desired material, viscous and yellow in color.

EXAMPLE 28

Amino Amide Acetal-5-(2,6-Dimethyl-tetrahydro-oxazolo[2,3-b]oxazol-7a-yl)-pentamine 6-Aminocapronitrile (N112) (32.72 g, 0.292 mol), diisopropanol amine (38.86 g, 0.292 mol) and zinc acetate dihydrate (1.60 g, 0.007 mol) were added to an oven dried three neck flask equipped with a stirrer and a nitrogen bleed into the reaction mixture. The resulting mixture was heating to 130–140° C. After ~one hour an aliquot for NMRs was taken (which show almost no reaction at this point). After ~18 hours another NMR aliquot was taken—which showed almost the complete conversion of the nitrile to amide acetal. Attempted fractional distillation of this material gave the following:

| Fraction | Head Temp. (° C.) | Pot. Temp. (° C.) | Press. (torr) | Comments |
|---|---|---|---|---|
| 1 | 93 | 127 | 1.6 | di-isopropanolamine |
| 2 | 93–102 | 136 | 1.7 | di-isopropanolamine |
| 3 | 102–107 | 145 | 1.8 | mostly di-isopropanolamine |
| 4 | 107–192 | 199 | 2.0–2.9 | All three materials - mostly amide acetal |
| Pot | — | — | — | All of the desired amide acetal |

EXAMPLE 29

Imino Amide Acetal-[5-(2,6-Dimethyl-tetrahydro-oxazolo[2,3-b]oxazol-7a-ylpentyl]isobutylidene-amine

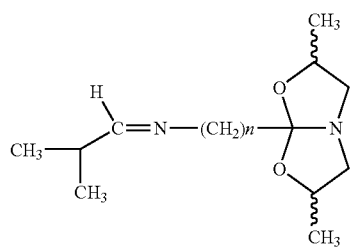

Di-isopropanolamine (70.33, 0.529 mol), 6-isobutylideneaminohexanenitrile (85.0 g, 0.50 mol), and zinc acetate dihydrate (2.7375 g, 0.0125 mol) were placed in an oven dried round bottom flask equipped with stirrer, reflux condenser, and a nitrogen bleed. The reaction content was heated to 140–145° C. for ~44 hours. The resulting material was cooled to room temperature and fractionally vacuum distillation apparatus:

| Fraction | Head Temp. (° C.) | Pot. Temp. (° C.) | Press. (torr) | Wt (g) | Comments |
|---|---|---|---|---|---|
| 1 | 65 | 101 | 1.4 | 18.80 | |
| 2 | 65–75 | 101–120 | 1.5 | 25.49 | |
| 3 | 75–92 | 120–140 | 1.5 | 12.01 | |
| 4 | 92–131 | 140–190 | 1.7 | 7.05 | |
| 5 | 131–134 | 190–190 | 1.7–2.3 | 23.33 | (all product) |
| 6 | 135–135 | 190–200 | 2.3–3.2 | 10.68 | (all product) |
| Pot | — | — | — | | desired material present |

EXAMPLE 30

Preparation of Amide Amide Acetals 5-cyanopentyl Hexaylamide (the amide resulting from the reaction of 6-amino-capronitrile and hexanoyl chloride) (52.5 g, 0.25 mol), diisopropanolamine (37.1 g, 0.2790 mol) and zinc acetate dihydrate (1.368 g, 0.0017 mol) were placed in an oven dried round bottom flask equipped with a stirring bar, a reflux condenser and a nitrogen bleed. The resulting mixture was heated to 140° C. for ~48 hours at which point the reaction was approximately 80% complete via NMRs analyses. Attempted fractional vacuum distillation of this material was unsuccessful at an oil temperature of 250° C. and under a vacuum of 0.0–1.2 torr.

EXAMPLE 31

Preparation of 1-Aza-(3-(tris-ethoxy-silyl)-propane)-4,6-dioxabicyclo[3,3,0]octane Diethanolamine (1.84 mol, 193.5 g) was charged into a 1000 ml flask under nitrogen. Diethyl zinc (0.092 mol, 11.36 g) was added into the same flask. Precipitation was observed. To this mixture tris-ethoxysilyl-propanenitrile (1.84 mol, 400.0 g) was added. The reaction was maintained at 90° C. for 65 hrs, then the temperature was raised to 100° C. for 48 hrs, finally the temperature was raised to 110° C. for 12 hrs. The formation of ammonia was detected during the reaction. Samples of the reaction mixture were taken and analyzed by GC. Once further increase of the reaction product was not observed the reaction was stopped, cooled to room temperature and extracted with petroleum ether (9×) to obtain the tris-ethoxysilyl-propanenitrile and the product amide ecetal as a mixture. The extraction solvent was removed in vacuo. Then the product was distilled to obtain 5.0 g of the final product with a purity of 92%.

EXAMPLE 32

Preparation of 1-Aza-(3-(tris-methoxy-silyl)-propane)-4,6-dioxabicyclo[3,3,0]octane Diethanolamine (2.28 mol, 240 g) was charged into a 1000 ml flask, under nitrogen, followed by diethyl zinc (0.11 mol, 14.09 g). Precipitation was initially observed. To this tris-methoxysilyl-propanenitrile (2.28 mol, 400.0 g) was added. The reaction mixture was heated to 100° C. Samples were taken every 8 hrs and analyzed by GC. After a reaction time of about 64 hours the reaction was stopped and the product isolated. The product was extracted with petroleum ether (9×) to obtain the tris-methoxysilyl-propane-nitrile and the product amide acetal as a mixture. The extraction solvent was removed in vacuo. Then, the product was distilled to obtain 87 g (~80 ml) of the final product with a purity of 98.2%. The sample was submitted for GC and NMR analysis.

EXAMPLES 33 AND 34

Coatings Made from Silanated Amide Acetals

| | EXAMPLE | |
|---|---|---|
| | 33 | 34 |
| Portion 1 | | |
| Example 31 (triethoxyl silinated amide acetal) | 6.0 | 0 |
| Example 32 (trimethoxyl silinated amide acetal) | 0 | 17.14 |
| diisobutyl ketone | 1.16 | 3.87 |
| Flow Additive* | 0.15 | 0.46 |
| Catalyst solution** | 0.53 | 1.78 |
| Portion 2 | | |
| Desmodur XP2410*** | 6.0 | 20.0 |
| Desmodur Z4470 BA**** | 3.67 | 12.25 |
| diisobutyl ketone | 0.73 | 2.42 |

-continued

|  | EXAMPLE | |
| --- | --- | --- |
|  | 33 | 34 |
| Portion 3 | | |
| 25% Nacure XP-221 in isopropanol***** | 0.48 | 1.70 |

*20% BYK 301 ® flow additive, supplied by BYK-CHEMIE, in Propylene glycol monomethyl ether acetate
**10% Di butyl tin dilaurate, supplied by Elf-Atochem North America, in ethyl acetate
***Desmodur XP2410 Trimer of Hexamethylene Diisocyanate from Bayer
****Desmodur Z4470 BA-Trimer of Isophorone Diisocyante in Butyl acetate from Bayer
*****Nacure XP-221-Dodecyl benzene sulfonic acid from King Industries For each of Examples 33 and 34, the constituents of Portion 1 were charged into a mixing vessel in the order shown above and mixed then Portion 2 was premixed and charged into the mixing vessel and thoroughly mixed with Portion 1, Portion 3 was then added with mixing. Each of the coating compositions was applied with a doctor blade over a separate phosphated cold roll steel panel primed with a layer of PowerCron® Primer supplied by PPG, Pittsburgh, Pa., to a dry coating thickness of about 50 micrometers and air dried at ambient temperature conditions. In example 34, a second set of coated panels was baked for 20 minutes at 60° C. Then the panels were tested using the test set forth in following table and the results of the test are shown in the attached table.

These results show that silanated amide acetals, crosslinked by isocyanates, gave excellent low VOC coatings which remain fluid for long periods of time. The coatings exhibited excellent early cure (as exhibited by good MEK rubs, low early swell ratios, and short BK3 times), both at ambient conditions and when cured at 60° C. The final cured coatings, after 30 days at ambient conditions, showed an excellent balance of hardness (>100 N/mm²) and mar resistance (rating >8). This type of mar rating for hard, ambient cured, coatings was exceptionally good, and demonstrated a very critical property for Refinish customers.

|  | Example #33 | Example #34 |
| --- | --- | --- |
| Calculated weight solids | 79.2 | 77.5 |
| TIME TO GEL | Fluid @ 1 Day, Gel @ 2 Days | Fluid @ 1 Day, Gel @ 2 Days |
| BK3 TIME(min) | 75.6 | 87.4 |
| BK4 TIME(min) | 357 | 376 |
| WATER SPOT | | |
| 4 HR @ room Temp | 7 | 7 |
| 1 Day @ room temp | 7 | 7 |
| 20 min @ 60 C. - on cool down |  | 6 |
| 20 min @ 60 C. - after 1 day |  | 7 |
| MEK RUBS | | |
| 4 HR @ room Temp | 600 | 700 |
| 1 Day @ room temp | 700 | 500 |
| 30 days@ room temp | 700 | 700 |
| 20 min @ 60 C. - on cool down |  | 750 |
| 20 min @ 60 C. - after 1 day |  | 750 |
| 20 min @ 60 C. - after 30 days |  | 700 |
| SWELL RATIO | | |
| 1 Day @ room temp | 2.27 | 1.79 |
| 7 days@ room temp | 2.01 | 1.51 |
| 30 days@ room temp | 1.42 | 1.37 |
| 20 min @ 60 C. - on cool down |  | 1.74 |
| 20 min @ 60 C. - after 1 day |  | 1.35 |
| 20 min @ 60 C. - after 7 days |  | 1.31 |
| 20 min @ 60 C. - after 30 days |  | 1.3 |
| GEL FRACTION | | |
| 30 days@ room temp | 94.96 | 94.57 |
| 20 min @ 60 C. - after 30 days |  | 95.69 |
| PERSOZ HARD | | |
| 4 HR @ room Temp | 30 | 19 |
| 1 Day @ room temp | 54 | 47 |
| 20 min @ 60 C. - on cool down |  | 21 |
| FISHER HARDNESS | | |
| 1 Day @ room temp | 7.3 | 6.89 |
| 7 days@ room temp | 48 | 63 |
| 30 days@ room temp | 109 | 113 |
| 20 min @ 60 C. - on cool down |  | 5.74 |
| 20 min @ 60 C. - after 1 day |  | 87.2 |
| 20 min @ 60 C. - after 7 days |  | 152 |
| 20 min @ 60 C. - after 30 days |  | 134 |
| Mar Resistance | | |
| Wet - 30 days @Room Temp | 8.5 | 8.5 |
| Dry - 30 days @Room Temp | 10 | 9.5 |
| Wet - 20 min @ 60 C. - after 30 days |  | 8.5 |
| Dry - 20 min @ 60 C. - after 30 days |  | 9.5 |

Swell Ratio

The swell ratio of a free film of the material made as described above (removed from a sheet of TPO—thermoplastic olefin) was determined by swelling the film in methylene chloride. The free film was placed between two layers of aluminum foil and using a LADD punch, a disc of about 3.5 mm in diameter was punched out of the film and the foil was removed from the film. The diameter of the unswollen film ($D_o$) was measured using a microscope with a 10× magnification and a filar lens. Four drops of methylene chloride were added to the film and the film was allowed to swell for a few second and then a glass slide was placed over the film and the swollen film diameter ($D_s$) was measured. The swell ratio was then calculated as follows:

$$\text{Swell Ratio} = (D_s)^2/(D_o)^2$$

Persoz Hardness Test

The change in film hardness of the coating was measured with respect to time by using a Persoz hardness tester Model No. 5854 (ASTM D4366), supplied by Byk-Mallinckrodt, Wallingford, Conn. The number of oscillations (referred to as Persoz number) were recorded.

Hardness (Fischer)

Hardness was measured using a Fischerscope® hardness tester (the measurement is in Newtons per square millimeter).

MEK Solvent Resistance Test

A coated panel was rubbed (100 times) with an MEK (methyl ethyl ketone) soaked cloth using a rubbing machine and any excess MEK was wiped off. The panel was rated from 1–10. A rating of 10 meant no visible damage to the coating; 9 meant 1 to 3 distinct scratches; 8 meant 4 to 6 distinct scratches; 7 meant 7 to 10 distinct scratches; 6 meant 10 to 15 distinct scratches with slight pitting or slight loss of color; 5 meant 15 to 20 distinct scratches with slight to moderate pitting or moderate loss of color; 4 meant scratches start to blend into one another; 3 meant only a few undamaged areas between blended scratches; 2 meant no visible signs of undamaged paint; 1 meant complete failure, i.e., bare spots were shown. The final rating was obtained by multiplying the number of rubs by the rating.

Water Spot

Water spot rating is a measure of how well the film is crosslinked early in the curing of the film. If water spot damage is formed on the film, this is an indication that the cure is not complete and further curing of the film is needed before the film can be wet sanded or buffed or moved from the spray both. The water spot rating was determined in the following manner.

Coated panels were laid on a flat surface and deionized water was applied with a pipette at 1 hour timed intervals. A drop about ½ inch in diameter was placed on the panel and allowed to evaporate. The spot on the panel was checked for deformation and discoloration. The panel was wiped lightly with cheesecloth wetted with deionized water, which was followed by lightly wiping the panel dry with the cloth. The panel was then rated on a scale of 1 to 10. Rating of 10 best—no evidence of spotting or distortion of discoloration; rating 9—barely detectable; rating 8—slight ring; rating 7—very slight discoloration or slight distortion; rating 6—slight loss of gloss or slight discoloration; rating 5—definite loss of gloss or discoloration; rating of 4—slight etching or definite distortion; rating of 3—light lifting, bad etching or discoloration; rating of 2—definite lifting; and rating of 1—dissolving of the film.

BK Time

Surface drying times of coated panels were measured according to ASTM D5895.

Gel Fraction

Gel fraction was measured according to the procedure set forth in U.S. Pat. No. 6,221,494 col. 8 line 56 to col. 9 line 2 which procedure is hereby incorporated by reference.

Time to Gel

The time it takes for a liquid coating to gel.

Wet Mar Resistance

The surface of a panel was marred using a 3% slurry of aluminum oxide in water and a felt pad. The marring was accomplished using a Daiei® Rub Tester. The test used 10 cycles with a weight of 500 grams. The rating shown was on a scale of 1 to 10 with 10 being no marring observed and 1 being very severe marring.

Dry Mar Resistance

The surface of a panel was marred using Bon Ami® Cleanser and a felt pad. The marring was accomplished using a Daiei® Rub Tester. The test used 15 cycles with a weight of 700 grams. The rating shown was on a scale of 1 to 10 with 10 being no marring observed and 1 being very severe marring.

COMPARATIVE EXAMPLE

Product I:

To a 3 liter glass round bottom flask was added 795.6 g of 2-ethyl-2-oxazoline and 1.56 g of LiCl. While these contents were held at 120 C, 501 g of Cardura E10 (Shell Chemicals, Houston, Tex.) was added dropwise over a 3.5-hour period. The contents were held for an additional 8.75 hours at 120 C to achieve a Cardura E 10 conversion of 82.2%. The batch was distilled beginning at 121.5 C and 399 mm Hg and finishing at 172 C and 1 mm Hg to recover 595.7 g of 2-ethyl-2-oxazoline and 597.6 g of product. The overall percent mass balance error was −0.47. Due to the dark yellow color of the product, it was redistilled at comparable conditions to yield a product with a color of 10 Hazen.

Product II:

To a 3 liter glass round bottom flask was added 1075.9 g of 2-ethyl-2-oxazoline and 2.09 g of LiCl. While these contents were held at 120 C, 675 g of Cardura E10 was added dropwise over a 3.9-hour period. The contents were held for an additional 9.5 hours at 120 C to achieve a Cardura E 10 conversion of 90.1%. The batch was distilled beginning at 77.9 C and 74.3 mm Hg and finishing at 167 C and 0.8 mm Hg to recover 795.5 g of 2-ethyl-2-oxazoline and 917.3 g of product. The overall percent mass balance error was −1.96. Without a second distillation, the product was very yellow.

Product III:

Undecyl amide acetal was prepared according to the procedure shown in Example 4 above.

|  |  | A | B | C |
|---|---|---|---|---|
| part 1 |  |  |  |  |
| Product I | cardura E-10 amide acetal |  | 34.83 |  |
| Product II | cardura E-10 amide acetal distilled |  |  | 32.22 |
| Product III | undecyl amide acetal | 32.22 |  |  |
| PM acetate |  | 6.44 | 6.97 | 6.44 |
| !0% DBTDL in ethyl acetate |  | 2.97 | 2.98 | 2.97 |
| Byk 306 |  | 0.43 | 0.47 | 0.43 |
| Byk-361 |  | 0.15 | 0.17 | 0.15 |
| Part 2 |  |  |  |  |
| desmodur Z4470BA |  |  | 20.41 | 19.29 |
| Desmodur XP2410 |  |  | 33.34 | 31.49 |
| diisobutyl ketone |  |  | 4.03 | 3.81 |
| Part 3 |  |  |  |  |
| acetic acid |  |  | 0.24 | 0.24 |
|  | H$_2$O spots 2 hr |  | 7 | 4 |
|  | H$_2$O spots 4 hd |  | 6 | 5 |

-continued

|  | A | B | C |
|---|---|---|---|
| H$_2$O spots 1 day | 10 | 10 | |
| Fischerscope hardness 30 days | 53 | 61 | |
| gel fraction 30 days after 140 F. × 20 min bake | 88 | 83 | |
| Tg in C. at 30 days after 140 F. × 30 min bake measured using differential scanning calorimetry (DSC, available from TA Instruments, New Castle, DE) | 52 | 34 | |
| APHA color of part 1 initial | 33 | 107 | 111 |
| APHA color of part 1 after 4 weeks at 120 F. | 88 | 196 | 257 |

The ingredients in part 1 were combined in a glass container then the ingredients in part 2 were added and stirred, and finally part 3 was added with mixing. The samples were drawn down to give coatings of ~2 mil in thickness. Water drops were placed on the coating at 2 and 4 hrs, and after 1 day at ambient temperature. The indentation hardness was read after 30 days at room temperature. The gel fraction was measured after a short bake (140 F×20 min) followed by storage at 30 days at RT. The hardnesses and water spot of the 2 samples were comparable. The gel fraction of the cardura E-10 sample was considerably lower than that of the undecyl amide acetal. The Tg of this sample was also much lower. A significant advantage of the amide acetals of this invention (Product III) is the low color, both initially and upon aging when compared to the conventional amide acetals of Product I and II. The APHA color was measured using a liquid color spectrophotometer such as BYK-Gardner LCS Cat. No. LCR-9500, available from Byk-Gardner, Columbia, Md., or equivalent.

EXAMPLE 35

Effect of Isocyanate on Strike-In

As listed below, Part 2 was added to Part 1 and then Part 3 was added with mixing. All the experimental formulations had a 1.15NCO/OH and a 70/30 mixture of HDI/IPDI. The commercial clearcoat control was 3800S, available from DuPont, Wilmington, Del., and was activated 3/1 by volume with XK205, also available from DuPont, Wilmington, Del.

The following clearcoats were sprayed over Centari 6000 silver metallic basecoat, available from DuPont, Wilmington, Del. on a phosphated cold roll steel panel primed with a layer of PowerCron® Primer supplied by PPG, Pittsburgh, Pa. There was a 30 min flash off of the basecoat at room temperature, before application of the clearcoats. The clearcoats were applied via 1 coat with a Devillbiss HVLP spraygun, with a gravity feed. After application of the clearcoats, there was a 15-minute flashoff time and the panels were baked at 60 C for 30 minutes.

Referring to the table below, the following materials were used as received:

Byk 361 is an acrylic leveling agent available from Byk-Chemie

Byk 358 is an acrylic leveling agent available from Byk-Chemie

Byk 310 is a silicon surface additive available from Byk-Chemie

DBTDL, dibutyl tin dilaurate, available from AKCROS Chemicals (Tinstab BL277).

Desmodur XP2410 is the asymmetric trimer of HDI available from Bayer with a viscosity of 700 cps DesmodurN 3600 is the trimer of HDI available from Bayer with a viscosity of 1200 cps DesmodurN 3300 is the trimer of HDI available from Bayer with a viscosity of 3000 cps Vestanat T 1890 L is 70% solids IPDI trimer in butyla acetate/Solvesso 100 (½) available from Degussa.

Description of Methods Used:

The potlife is defined as the period of time during which the clearcoat is still relatively easy to spray. The potlife of the compositions was measured by measuring the viscosity increase as a function of time. The generally accepted definition of the potlife time of a clearcoat is the time between when the clearcoat is at its initial viscosity until it is at twice its initial viscosity.

Dry film thickness was measured using equipment from Braive Instruments, Belgium, with an accuracy of 0.001 mm.

Tack free time was measured according to ASTM D1640, p. 273. A film is considered to have dried "tack-free" when the tack tester tips over immediately on removing a 300 g weight allowed to act for 5 sec on the counter-weighted metal square base fitted with masking tape and aluminum foil.

Gloss is measured using a glossmeter and recording the specular reflection at a particular angle (in this case, 20°). The reflectometer used was REF03, Dr. Lange, Germany.

Distinctness of Image (DOI) was measured with a Wavescan-DOI apparatus from BYK Gardner, Germany. The DOI of a clearcoat can also be described in terms such as brilliance, sharpness or clarity. The more distinct the reflection of an object on the surface, the more brilliant the coating film will appear.

Strike-in is the interaction between the basecoat and clearcoat, during wet-on-wet application. The degree of interaction is dependent upon the formulation, process parameters and/or ambient conditions. When this interaction is excessive, strike-in, or redissolving, will occur. This will result in a mottled appearance of the basecoat and a "fuzzy" appearance of the clearcoat. Thus, it is critical to minimize this strike-in to maximize appearance. The degree of strike-in can be expressed by measuring the "flop index" or "flop" of a panel. The lower the flop measurement, the greater the strike-in. The flop of the samples below was measured on the same day as the basecoat-clearcoat application with a Chromavision MA100, available from DuPont, Wilmington, Del. The measurements were compared to those of a standard reference panel sprayed with 3800S, which was sprayed under the same spray and bake conditions.

| Clearcoats | A | B | C | 3800S (control) |
|---|---|---|---|---|
| Part 1 | | | | |
| Undecyl amide acetal | 20 | 20 | 20 | |
| 10% DBTDL in xylene | 1.34 | 1.36 | 1.396 | |
| BYK 361 | 0.89 | | | |
| BYK 358 | | 0.171 | 0.179 | |
| BYK 310 | 0.110 | 0.110 | 0.110 | |
| PM Acetate | 2.85 | 2.80 | 2.90 | |
| Part 2 | | | | |
| Desmodur XP2410 | 18.5 | | | |
| Desmodur N3600 | | 18.99 | | |
| Desmodur N3300 | | | 19.9 | |
| VESTANAT T 1890L | 11.33 | 11.63 | 12.17 | |
| Part 3 | | | | |
| Acetic Acid | 0.433 | 0.433 | 0.433 | |
| Results | | | | |
| Solids | 81.5% | 81.6% | 81.6% | 53.6% |
| Potlife | >5 hrs | >5 hrs | >5 hrs | 1 hr |
| Thickness, μm | 80 | 80 | 80 | 70 |
| Tack Free Time, min | 10 | 10 | 10 | 10 |
| Gloss, 20° | 82 | 82 | 87 | 91 |
| DOI | 90 | 91 | 90 | 85 |
| Flop | 8.68 | 8.85 | 9.01 | 8.79 |

As seen in the above table, the clearcoat made with a more viscous isocyanate (Desmodur N3600 or Desmodur N3300) gave a higher flop than the reference 3800S. The higher flop indicates that there is less strike-in of the amide acetal clearcoat, when applied over Centari 6000. The amide acetal-based clearcoat of this invention exhibits a favorably low level of strike-in.

What is claimed is:

1. An amide acetal composition, comprising:

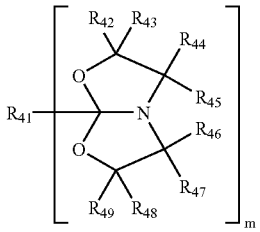

wherein $R_{41}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, nitrile, imino, amino, alkylamino, dialkylamino, cyano, alkoxy silane, hydroxyl, methacryloxy isocyanato, urethane, amide acetal (multifunctional) and carbamoyl, and wherein m is greater than or equal to 3.

2. A coating composition comprising the composition of claim 1.

3. The coating composition of claim 2 further comprising a crosslinking group.

4. The coating composition of claim 3, wherein the crosslinking group is selected from the group consisting of isocyanates epoxides, carboxylic acid anhydrides, melamine and silane(s).

5. An amide acetal composition, comprising:

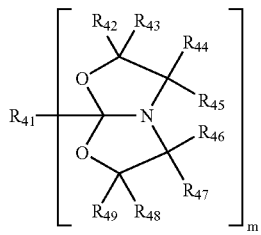

wherein $R_{42}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, nitrile, imino, amino, alkylamino, dialkylamino, cyano, alkoxy silane, hydroxyl, methacryloxy isocyanato, urethane, amide acetal (multifunctional) and carbamoyl, and wherein $R_{41}$ is an alkoxy silane group having the structure $R_{50}$—Si[O(CH$_2$)$_p$H]$_3$, where each p is independently 1 to 10, and $R_{50}$ is independently selected from the group consisting of $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, and $C_1$–$C_{20}$ aralkyl and m=1 to 4.

6. A coating composition comprising the amide acetal of claim 5.

* * * * *